US012138138B2

(12) United States Patent
Jang

(10) Patent No.: US 12,138,138 B2
(45) Date of Patent: Nov. 12, 2024

(54) DENTAL IMPLANT ABUTMENT WITH ENHANCED SHOCK DISTRIBUTION FUNCTION

(71) Applicant: Cheon Seok Jang, Ansan-si (KR)

(72) Inventor: Cheon Seok Jang, Ansan-si (KR)

(*) Notice: Subject to any disclaimer, the term of this patent is extended or adjusted under 35 U.S.C. 154(b) by 378 days.

(21) Appl. No.: 17/765,698

(22) PCT Filed: Oct. 21, 2020

(86) PCT No.: PCT/KR2020/014377
§ 371 (c)(1),
(2) Date: Mar. 31, 2022

(87) PCT Pub. No.: WO2021/091125
PCT Pub. Date: May 14, 2021

(65) Prior Publication Data
US 2022/0338963 A1 Oct. 27, 2022

(30) Foreign Application Priority Data
Nov. 7, 2019 (KR) .................. 10-2019-0141914

(51) Int. Cl.
*A61C 8/00* (2006.01)
*A61K 6/15* (2020.01)
*A61K 6/898* (2020.01)

(52) U.S. Cl.
CPC .......... *A61C 8/0012* (2013.01); *A61C 8/0057* (2013.01); *A61C 8/0065* (2013.01);
(Continued)

(58) Field of Classification Search
CPC ... A61C 8/0012; A61C 8/0057; A61C 8/0065; A61C 8/0069; A61C 8/0086; A61K 6/15;
(Continued)

(56) References Cited

U.S. PATENT DOCUMENTS 5,425,639 A * 6/1995 Anders ................ A61C 8/0086
433/169
11,950,980 B1 * 4/2024 Kim ..................... A61C 8/0075
(Continued)

FOREIGN PATENT DOCUMENTS

KR 10-2010-0138504 A 12/2010
KR 10-2014-0026132 A 3/2014
(Continued)

*Primary Examiner* — Matthew M Nelson
(74) *Attorney, Agent, or Firm* — KORUS Patent, LLC; Seong Il Jeong

(57) ABSTRACT

An implant abutment according to the present invention is a dental implant abutment with an enhanced shock distribution function, the dental implant abutment comprising: an upper coupling portion that is an upper portion coupled to an artificial tooth; a lower coupling portion that is a lower portion coupled to a fixture, and an exposed portion that is exposed to the outside between the upper coupling portion and the lower coupling portion and has a plurality of flow grooves. By forming a plurality of grooves in the exposed portion of the implant abutment, the exposed portion of the implant abutment performs a shock distribution function as if it shakes elastically and distributes an occlusal force of teeth exerted to the implant, thereby providing a buffering function of relieving an impact on an area where the implant is inserted.

6 Claims, 6 Drawing Sheets

(52) U.S. Cl.
CPC .......... *A61C 8/0069* (2013.01); *A61C 8/0086* (2013.01); *A61K 6/15* (2020.01); *A61K 6/898* (2020.01)

(58) Field of Classification Search
CPC  A61K 6/71; A61K 6/898; A61L 27/20; A61L 27/50; A61L 2430/12
USPC ......................................................... 433/173
See application file for complete search history.

(56) References Cited

U.S. PATENT DOCUMENTS

| | | | | |
|---|---|---|---|---|
| 2003/0124488 A1* | 7/2003 | Gittleman | ............ | A61C 8/0065 |
| | | | | 433/173 |
| 2006/0014120 A1* | 1/2006 | Sapian | ................ | A61C 8/0057 |
| | | | | 433/169 |
| 2007/0099151 A1* | 5/2007 | Ilan | ...................... | A61C 8/0053 |
| | | | | 433/173 |
| 2010/0255447 A1* | 10/2010 | Biris | .................... | A61L 27/306 |
| | | | | 523/105 |
| 2014/0030675 A1* | 1/2014 | Sanchez | ............... | A61C 8/0012 |
| | | | | 433/174 |
| 2014/0315151 A1* | 10/2014 | Yagami | .................. | A61C 13/08 |
| | | | | 433/201.1 |
| 2016/0262855 A1* | 9/2016 | Ju | ........................ | A61C 8/0074 |
| 2018/0000562 A1* | 1/2018 | Jang | ......................... | A61C 5/70 |
| 2018/0235736 A1* | 8/2018 | Lee | ...................... | A61C 8/0062 |
| 2019/0053880 A1* | 2/2019 | Lin | ...................... | A61C 8/0086 |
| 2022/0023011 A1* | 1/2022 | Dagher | ................. | A61C 8/0054 |
| 2022/0338963 A1* | 10/2022 | Jang | ........................ | A61L 27/50 |
| 2023/0248482 A1* | 8/2023 | Vachtenberg | ........ | A61C 8/0024 |
| | | | | 433/174 |
| 2024/0122681 A1* | 4/2024 | Toscano | ............... | A61C 8/0054 |

FOREIGN PATENT DOCUMENTS

| | | | | |
|---|---|---|---|---|
| KR | 10-2016-0038330 A | | 4/2016 | |
| KR | 10-1981778 B1 | | 5/2019 | |
| KR | 2080448 B1 | * | 2/2020 | ........... A61C 8/0012 |
| KR | 2020020025 A | * | 2/2020 | ........... A61C 8/0057 |
| WO | WO-2016098921 A1 | * | 6/2016 | ......... A61C 13/1026 |

* cited by examiner

DENTAL IMPLANT ABUTMENT WITH ENHANCED SHOCK DISTRIBUTION FUNCTION

FIELD OF THE INVENTION

The present invention relates to a dental implant abutment with an enhanced shock distribution function, and more particularly, to a dental implant abutment with an enhanced shock distribution function that allows an exposed portion of the abutment, which is not covered by an artificial tooth and a fixture, to distribute an occlusal force of teeth.

BACKGROUND OF THE INVENTION

A dental implant surgery is a treatment method in which an implant made of a strong and biocompatible material such as titanium is placed in the gum bone of a lost tooth, and an artificial tooth is mounted on it to recover the shape and function similar to natural teeth. In general, an implant may be composed of an artificial tooth, an abutment, and a fixture. The fixture is a part that is inserted and fixed into the gum bone, and the abutment is a part that connects the artificial tooth and the fixture. Although the implant can perform most of functions of natural teeth, it cannot reproduce inherent movements of natural teeth because the fixture and the gum bone must be tightly coupled to each other. Specifically, there is a problem that the implant does not have a buffering function, which is served by a periodontal ligament around the natural tooth, against a force exerted to the natural tooth by an occlusal force of teeth.

According to Korean Patent No. 10-1981778 "Abutment and Implant Including the Same," the patent provides an abutment including: a central portion placed in a fixture; an upper portion disposed on an upper surface of the central portion to which a crown is fastened; a lower portion disposed on a lower surface of the central portion and having a groove portion formed on a side surface thereof; and a fixing portion rotatably introduced into the groove portion so as to be extendable to the outside of the lower portion. In addition, the known patent discloses that the groove portion may include a first groove formed on one side of the lower portion and a second groove that is formed on the other side opposite to one side of the lower portion and that is communicated with the first groove inside the lower portion. Furthermore, the patent discloses that the fixing portion may include a first screw disposed in the first groove and having a screw thread formed on an outer circumferential surface thereof and a second screw disposed in the second groove and having a screw thread formed on an outer circumferential surface in such a way that the screw thread of the second screw is engaged with the screw thread of the first screw inside the lower portion. According to this structure, the known patent can promote strong coupling between the fixture and the abutment by including a fixing portion that can be extended from the side surface of the lower portion placed inside the fixture. In addition, since the abutment can be adjusted by a slight angle with respect to the fixture, the implant treatment can be effectively performed regardless of an oral structure. Furthermore, since a rotational and vertical movement of the abutment connected to the inside of the fixture is limited, the implant can have a strong fixing force.

However, this technology only strengthens a coupling force between the fixture and the abutment, and it does not provide a solution for distributing an occlusal force of teeth exerted to the artificial teeth as the problem mentioned above.

Therefore, there is an urgent need to develop a new and advanced implant that can firmly fix between the fixture and the gum bone and provide a function similar to a movement function of a natural tooth in response to an occlusal force of teeth exerted to an artificial tooth.

DETAILED DESCRIPTION OF THE INVENTION

Technical Problems

The present invention has been devised to overcome the problems of the technology mentioned above, and the main object of the present invention is to provide a function of distributing an occlusal force of teeth by forming a plurality of grooves in an exposed portion of an abutment that is not covered by an artificial tooth and a fixture.

Another object of the present invention is to provide a function of distributing an occlusal force of teeth in an oblique direction by forming a groove provided in an exposed portion of an abutment in a form of a screw thread.

Another object of the present invention is to provide a function of distributing an occlusal force of teeth in a horizontal direction by forming a plurality of grooves provided in an exposed portion of an abutment in a form of a slit.

An additional object of the present invention is to assist an elastic flow or movement of an abutment and a function of absorbing an external shock, by filling a flow groove of an abutment with fillers.

SUMMARY OF THE INVENTION

To achieve the object mentioned above, a dental implant abutment with an enhanced shock distribution function according to the present invention comprises: an upper coupling portion that is an upper portion coupled to an artificial tooth; a lower coupling portion that is a lower portion coupled to a fixture, and an exposed portion that is exposed to the outside between the upper coupling portion and the lower coupling portion and has a plurality of flow grooves.

In addition, the flow groove is characterized in that it is recessed in a form of a screw thread along an outer circumferential surface of the exposed portion.

Furthermore, the flow groove is characterized in that it includes a first slit recessed to a certain depth from an inner circumferential surface of the exposed portion to the outer circumferential surface of the exposed portion and a second slit recessed to a certain depth from the outer circumferential surface of the exposed portion to the inner circumferential surface of the exposed portion in a state of being spaced apart from the first slit by a certain height, and the first and second slit are alternately formed along a height direction of the exposed portion in a repeated way.

Technical Effects of the Invention

A dental implant abutment according to the present invention has the following technical effects.

1) By forming a plurality of grooves in the exposed portion of the implant abutment, the exposed portion performs a shock distribution function as if it shakes elastically, thereby providing a function of distributing an occlusal force of teeth exerted to the implant.
2) By forming a groove in the exposed portion in a form of a screw thread, the exposed portion has an oblique structure to bypass an occlusal force of teeth in an oblique direction, thereby providing a function of effectively distributing the occlusal force of teeth in the oblique direction.

3) By forming 3 to 4 grooves in the exposed portion in a form of a groove penetrating through the exposed portion, the grooves can provide a function of absorbing the occlusal force of teeth.
4) By forming grooves in the exposed portion in a form of a slit recessed along a horizontal direction of the exposed portion and arranging these slits to form a radial structure in the horizontal direction, an occlusal force of teeth can pass toward a radial direction, thereby providing a function of radially distributing the occlusal force of teeth in the horizontal direction.
5) By filling a flow groove of the abutment with filler, the filler can support an elastic movement of the abutment and assist a function of buffering an external shock.

DESCRIPTION OF MAIN REFERENCE NUMBERS IN THE DRAWINGS

Figure 1:
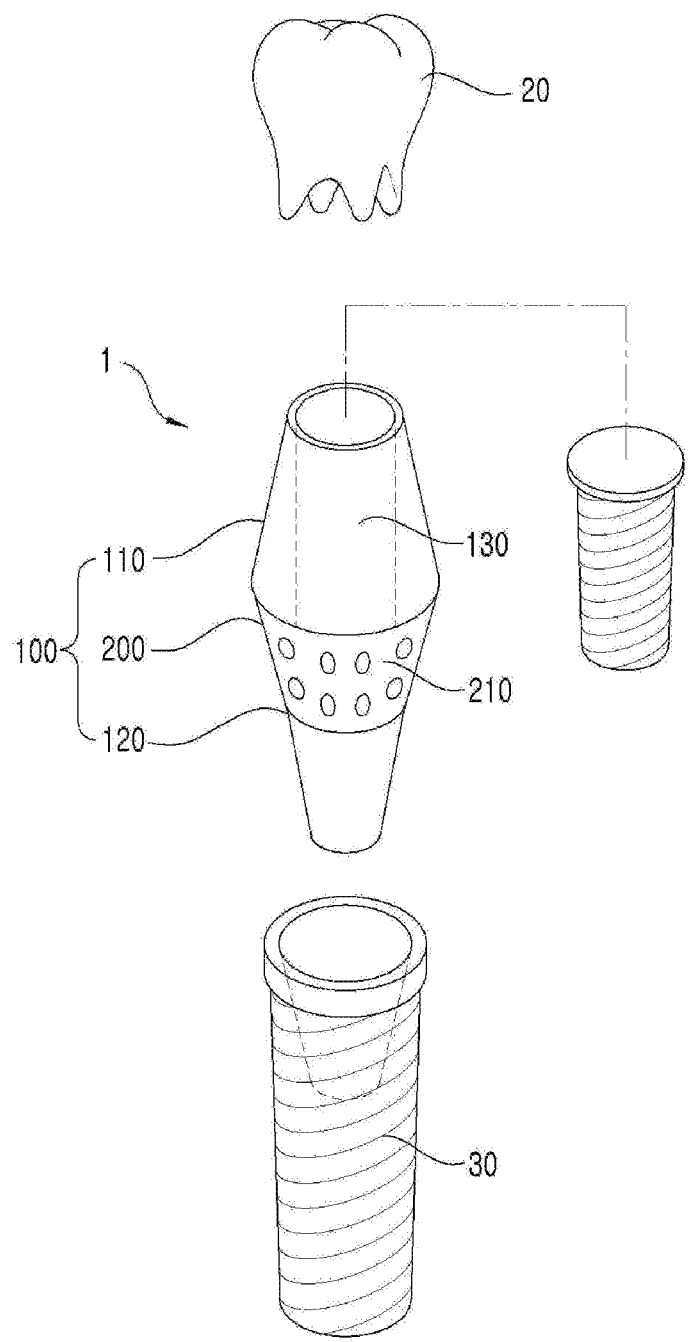
FIG. 1 is a perspective view illustrating an embodiment of an implant abutment according to the present invention.

1: implant
20: artificial tooth
30: fixture
100: abutment
110: upper coupling portion
120: lower coupling portion
200: exposed portion
130: hollow
140: expanded recessed portion
150: coupling groove
210: flow groove
220: thread
230: slit
231: first slit
232: second slit
240: horizontal slit
S100: a step of producing a first solution
S110: a step of producing a second solution
S120: a step of obtaining a first material
S130: a step of producing a third solution
S140: a step of obtaining a second material
S150: a step of drying
S160: a step of completing a filling solution

BEST MODE FOR THE INVENTION

The present invention is a dental implant abutment with an enhanced shock distribution function, the dental implant abutment comprises: an upper coupling portion that is an upper portion coupled to an artificial tooth; a lower coupling portion that is a lower portion coupled to a fixture, and an exposed portion that is exposed to the outside between the upper coupling portion and the lower coupling portion and has a plurality of flow grooves filled with filler, wherein the filler is a mixture of 10 to 30 wt % of a base material and 70 to 90 wt % of a filling solution containing sodium hyaluronate, based on a total weight of the filler, and the filling solution contains an elastic auxiliary agent containing 10 to 25 wt % of polycarbonate diol based on a total weight of the filling solution.

MODES FOR THE INVENTION

Hereinafter, preferred embodiments of the present invention will be described in detail with reference to the accompanying drawings. The accompanying drawings are not drawn to scale, and like reference numbers in each drawing refer to like elements.

FIG. 1 is a perspective view illustrating an embodiment of an implant abutment according to the present invention.

An implant 1 provides a function of replacing a tooth lost due to tooth cavity or gum disease by inserting an artificial tooth 20 into the gum. The implant 1 comprises an abutment 100 connected to the artificial tooth 20, the artificial tooth 20, and a fixture 30 inserted into a gum bone.

The artificial tooth 20 is an artificially formed tooth instead of a natural tooth and may be formed in various shapes to match a shape of a tooth to be treated. The fixture 30 is inserted into the gum to provide a function of firmly fixing the gum bone and the artificial tooth 20. The fixture 30 may be formed in a form of a screw thread similarly to a known fixture.

The present invention relates to the abutment 100 positioned between the artificial tooth 20 and the fixture 30. Similarly to a known abutment, an overall appearance of the abutment 100 is in a shape of a cylinder and has a hollow inside 130. The abutment 100 includes an upper coupling portion 110, a lower coupling portion 120, and an exposed portion 200.

First, the upper coupling portion 110 is a portion that forms an upper portion of the abutment 100 and is inserted and coupled to the inside of the artificial tooth 20. A lower portion of the upper coupling portion 110 is formed larger than an upper portion of the upper coupling portion 110. That is, it is desired that the upper coupling portion 110 is provided as a structure capable of stably supporting a weight of the artificial tooth 20 by having a cylindrical shape with a hollow 130 therein and a trapezoidal shape in a cross section.

The lower coupling portion 120 is a portion forming a lower portion of the abutment 100 and is a portion coupled to the fixture 30 inserted into the gum bone. The lower coupling portion 120 is formed in a shape corresponding to a hexagonal head formed on an upper end of the fixture 30 and can be mounted on the fixture 30. In addition, the hexagonal head of the fixture 30 and a hexagonal groove of the abutment 100 have holes with a size corresponding to a diameter of a screw, which is described later, so that the screw can be inserted through the holes. The hexagonal head and the hexagonal groove are only an example, and they may be formed in various other shapes.

As described above, the upper coupling portion 110 is covered by the artificial tooth 20, and the lower coupling portion 120 is covered by the fixture 30. In this case, a portion that is not covered between the upper and lower coupling portions 110, 120 is referred to as the exposed portion 200 in the present invention.

The exposed portion 200 is formed in a tapered shape so that a diameter gradually decreases from an upper portion of the exposed portion 200 to a lower portion of the exposed portion 200. Accordingly, the exposed portion 200 allows the upper coupling portion 110 to be naturally connected to the lower coupling portion 120, which is formed with a relatively smaller diameter than those of the upper coupling portion 110 and the lower portion of the upper coupling portion 110. This structure allows the exposed portion 200 to sufficiently supports a load of the artificial tooth 20 and ensures structural stability.

A method of implant surgery using the abutment 100 having the configurations mentioned above will be described as follows.

First, the fixture 30 is inserted into the gum bone, and then, positions of the abutment 100 and the fixture 30 are adjusted so that the hexagonal groove of the lower coupling portion 120 of the abutment 100 and the hexagonal head of the fixture 30 are engaged with and stably coupled to each other. Next, by penetrating the screw into a hollow 130 of the abutment 100 and tightening a head of the screw to be coupled with the hexagonal groove of the lower coupling portion 120, the abutment 100 and the fixture 30 do not rotate and are tightly coupled to each other. Lastly, by coupling the artificial tooth 20 to the upper coupling portion 110 of the abutment 100, the operation of the implant 1 may be generally completed.

Although the implant 1 can replace a function of the natural tooth, there is a problem in that it is difficult to reproduce an inherent movement of the natural tooth because the fixture 30 must be firmly fixed to the gum bone. To solve this problem, the present invention enhances an elasticity of the abutment 100 by providing the enhanced abutment 100, specifically by specializing the exposed portion 200 of the abutment 100.

Specifically, the exposed portion 200 described above is not covered by the artificial tooth 20 or the fixture 30 and is a portion that is more directly affected by an occlusal force of teeth exerted to the implant 1. Therefore, if the exposed portion 200 is formed as if it moves naturally and the occlusal force of teeth can be dispersed and distributed, it is possible to prevent cracks in the fixture 30 due to the occlusal force, as well as prevent a decrease in a coupling force between the exposed portion 200 and the fixture 30.

In order to form the exposed portion 200 to act as if it has elastic movement, the present invention may have a flow groove 210 in the exposed portion 200 as shown in FIG. 1.

A plurality of flow grooves 210 may be provided on an outer circumferential surface of the exposed portion 200 or may be provided in the hollow 130 located inside the abutment 100. By providing such a plurality of flow grooves 210 in the exposed portion 200, the exposed portion 200 can act as if it is shaken elastically and can provide a function of effectively distributing the occlusal force of teeth through the exposed portion 200.

First, the flow groove 210 may be formed to have a porous structure as shown in FIG. 1, which is a basic example of the flow groove 210 according to the present invention.

The flow grooves 210 forming the porous structure may be randomly disposed on a surface of the exposed portion 200. If the exposed portion 200 is made of a material having elasticity, the exposed portion 200 can flexibly stretch and contract, thereby distributing an occlusal force of teeth. If the abutment 100 including the exposed portion 200 is made of a metal material, which is common in general abutments, it may not stretch and contract flexibly as in the example described above. However, since an inherent bending property of metal induces the occlusal force of teeth into the porous structure, it can also serve to distribute the occlusal force of teeth through the exposed portion 200. In this case, since the occlusal force of teeth is exerted by a force that upper and lower teeth collide, it is generally exerted in a vertical direction, that is, in a longitudinal direction of the implant 1.

In other words, the flow groove 210 forming the porous structure provides a function of distributing the occlusal force of teeth exerted in the vertical direction into various directions using the bending property of metal and the presence of the flow groove 210 of the porous structure.

In addition, the flow groove 210 may be formed in a shape that is recessed to a certain depth or penetrates the exposed portion 200.

Specifically, when the flow groove 210 is formed in a shape recessed to a certain depth, the occlusal force of teeth exerted in the vertical direction of the implant 1 is concentrated on the flow groove 210, and stress may be generated in the flow groove 210. Accordingly, the flow groove 210 can slightly shake and/or vibrated, thereby providing a function of distributing and absorbing the occlusal force of teeth. In addition, the flow groove 210 formed in the recessed shape can basically guarantee a structural stability of the implant 1 and a supporting power of the exposed portion 200 at the same time, as compared to the flow groove 210 formed in a penetrating shape, which is described later.

Meanwhile, in case of the flow groove 210 formed to penetrate the exposed portion 200, the flow groove 210 may vibrate by the occlusal force of teeth exerted in the vertical direction of the implant 1 according to the same principle as described above. In addition, the flow groove 210 formed in a penetrating shape can further maximize movement. In this case, in order to compensate for the reduced supporting power of the exposed portion 200 by forming the flow groove 210 in a penetrating shape, the exposed portion 200 may be formed of a material having a rigid property, for example, a nitinol alloy.

As described above, the flow groove 210 of the present invention may be formed in a shape penetrating the exposed portion 200 as well as in a shape recessed to a certain depth.

In summary, the flow groove 210 in a recessed form or a penetrating form provides a characteristic capable of distributing and absorbing the occlusal force of teeth exerted to the implant 1.

Figure 2:
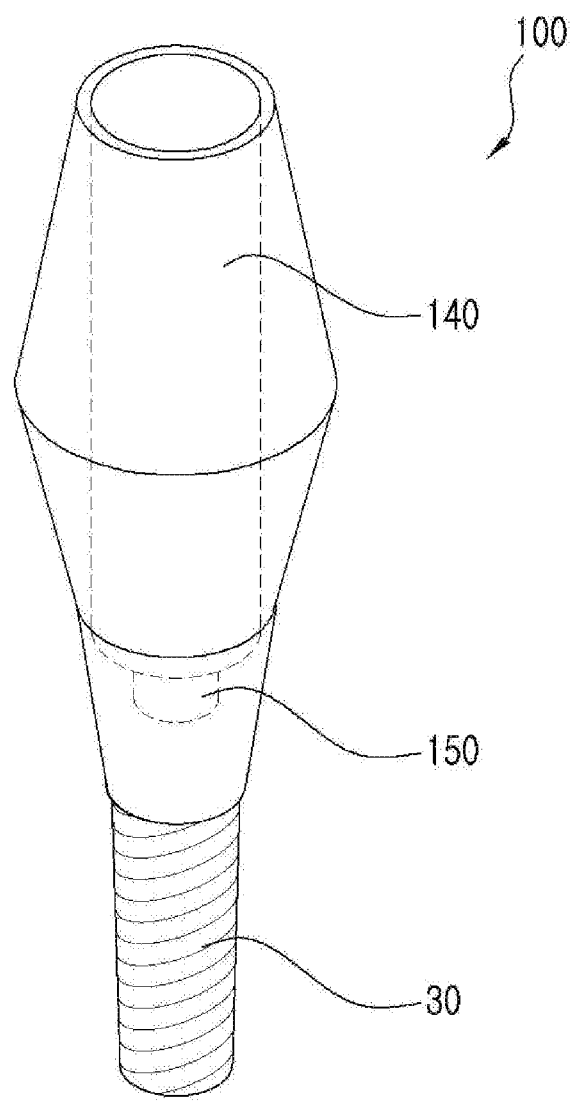
FIG. 2 is a perspective view illustrating another embodiment of an implant abutment according to the present invention.

FIG. 2 is a perspective view illustrating another embodiment of an implant abutment according to the present invention.

As can be seen from FIG. 2, the abutment 100 may be formed in a state of being combined with the fixture 30 through a screw, unlike in FIG. 1. This abutment 100 is called a one-piece type abutment 100.

A known one-piece type abutment may not separately include a screw for coupling the abutment and the fixture. This known one-piece type abutment may not have the hollow 130 formed therein. Alternatively, this known one-piece type abutment may be formed with a small, recessed groove recessed to approximately 1 to 12 mm toward the fixture 30 from an upper surface of the abutment, thereby providing a function of easily attaching to or detaching from the artificial tooth 20.

On the other hand, the one-piece type abutment 100 of the present invention shown in FIG. 2 may be provided with an expanded recessed portion 140 in which a recessed groove is extended to an area around a bottom surface of the exposed portion 200. In this case, the area around the bottom surface of the exposed portion 200 refers to a portion located at a height of the upper end of the fixture 30 when the abutment 100 is coupled to the fixture 30.

The expanded recessed portion 140 not only provides a function that can be easily attached to or detached from the artificial tooth 20 like the small, recessed groove mentioned above, but also forms an air layer inside the expanded recessed portion 140 when combined with the artificial tooth 20, and thus, the air layer can buffer an external force exerted to the artificial tooth 20.

In addition, a coupling groove 150 to which a driver can be applied may be formed on a bottom surface of the expanded recessed portion 140. The coupling groove 150 may be formed in a shape corresponding to the driver to be used.

Figure 3A:
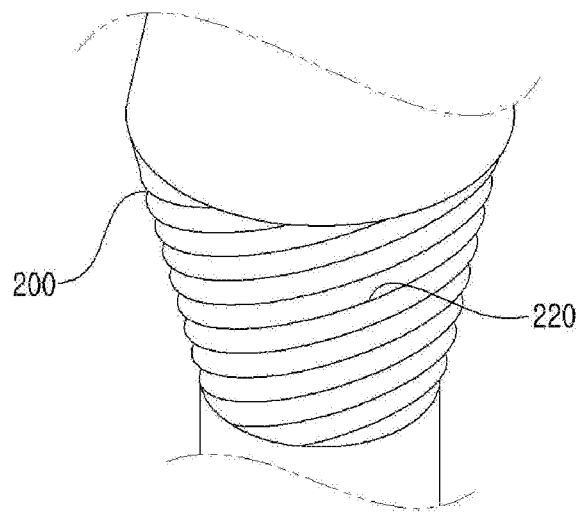
FIGS. 3A-3B are cross-sectional views illustrating a first modified embodiment of an implant abutment according to the present invention.
Figure 3B:
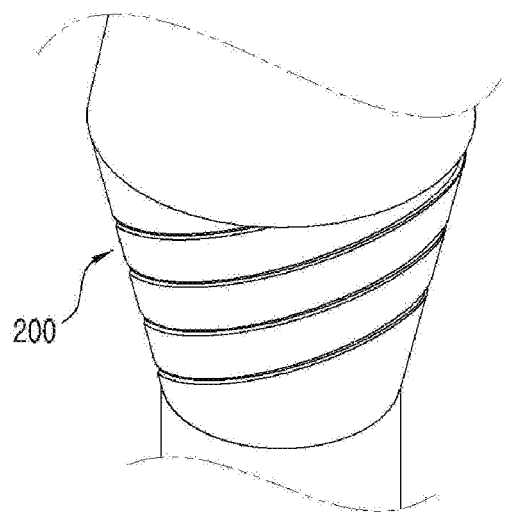

FIGS. 3A-3B are cross-sectional views illustrating a first modified embodiment of an implant abutment according to the present invention.

As can be seen from FIGS. 3A and 3B, the flow groove 210 according to FIGS. 3A and 3B is a groove recessed in a form of a screw thread 220.

The flow groove 210 according to FIGS. 3A and 3B extends from an upper portion of the exposed portion 200 to a lower portion of the exposed portion 200 in an oblique direction. In other words, the flow groove 210 according to FIGS. 3A and 3B has an inclined structure. Accordingly, when the occlusal force of teeth is exerted to the artificial teeth 20 in the vertical direction of the implant 1, the flow grooves 210 according to FIGS. 3A and 3B can bypass the occlusal force of teeth to an inclined direction of the flow grooves 210 of the exposed portion 200, specifically in a direction that is not perpendicular or parallel to the occlusal force of teeth.

More specifically, since the flow grooves 210 according to FIGS. 3A and 3B are formed of a plurality of inclined grooves along a longitudinal direction of the exposed portion 200, the occlusal force of teeth is repeatedly absorbed through each inclined groove while the occlusal force proceeds to and passes through the lower coupling portion 120. As a result, the flow groove 210 according to FIGS. 3A and 3B provides a function of efficiently distributing the occlusal force of teeth in the oblique direction.

In this case, the flow grooves 210 of FIG. 3A are formed in a greater number than the flow grooves 210 of FIG. 3B and more efficiently perform the function of absorbing and distributing the occlusal force of teeth.

That is, compared to the flow groove 210 of FIG. 3A, since the flow groove 210 of FIG. 3B is formed of 3 to 4, a structural stability can be ensured, as well as can absorb and distribute the occlusal force of teeth.

Furthermore, as described above with reference to FIG. 1, a structure of a screw thread 220 in the oblique direction of FIGS. 3A and 3B may be formed in a penetrating form. However, since the abutment 100 of FIG. 3B in which the flow grooves 210 are formed in a smaller number is structurally stable, it is more desired that the penetrating structure is applied to the abutment 100 shown in FIG. 3B.

Figure 4:
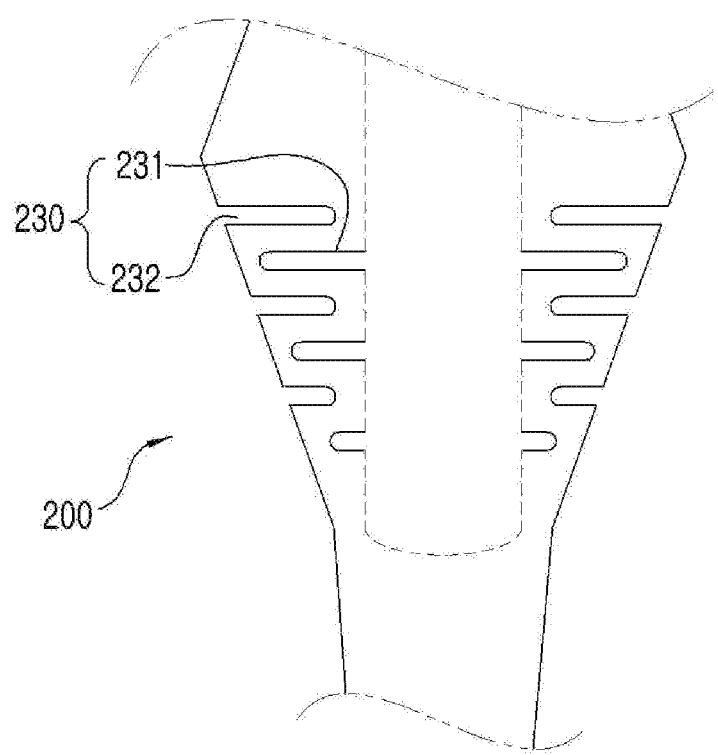
FIG. 4 is a cross-sectional view illustrating a second modified embodiment of an implant abutment according to the present invention.

FIG. 4 is a cross-sectional view illustrating a second modified embodiment of an implant abutment according to the present invention.

The flow groove 210 according to FIG. 4 is a groove recessed in a form of a slit 230. The groove formed on an inner circumferential surface of the exposed portion 200 is referred to as a first slit 231, and a groove formed on an outer circumferential surface of the exposed portion 200 is referred to as a second slit 232.

The first slit 231 is a flow groove 210 recessed to a certain depth from the inner circumferential surface of the hollow 130 toward the outer circumferential surface of the exposed portion 200 along the hollow 130, and the second slit 232 is a flow groove 210 recessed to a certain depth from the outer circumferential surface of the exposed portion 200 toward the hollow 130 along the outer circumferential surface of the exposed portion 200. The second slit 232 may be formed to be spaced apart by a certain height from the first slit 231. In this case, the first and second slit 231, 232 may have various shapes. In addition to those shown in the drawings, the first and second slit 231, 232 may be recessed in a rounded shape or a tapered shape.

The first and second slits 231, 232 may be alternately formed along a height direction of the exposed portion 200 in a repeated way. That is, in a cross-sectional view of the exposed portion 200, the first and second slit 231, 232 may be formed in a zigzag form.

In other words, a plurality of flow grooves 210 according to FIG. 4 are formed along a circumference of the exposed portion 200 and have a structure arranged in a zigzag form, that is, in a radial form, along the longitudinal direction of the exposed portion 200.

Meanwhile, the exposed portion 200 of the abutment 100 having such a structure may be divided into a structure formed of a rigid material that cannot elastically contract and a structure formed of a non-rigid material that can contract. Each structure will be described with respect to an occlusal force distributing function.

First, in case of the exposed portion 200 formed of a rigid material, when an occlusal force of teeth is transferred to the artificial tooth 20 in a vertical direction of the implant 1, the flow groove 210 according to FIG. 4 can pass the occlusal force of teeth in a radial form of the exposed portion 200, specifically, in a horizontal direction of the implant 1, which is perpendicular to a direction of the occlusal force of teeth.

More specifically, since the flow groove 210 according to FIG. 4 is arranged and formed in a zigzag form along the longitudinal direction of the exposed portion 200, both an occlusal force of teeth generated inside the exposed portion 200 and an external force exerted in the vertical direction of the implant 1 are passed into the horizontal direction of the implant 1 together. In other words, the flow groove 210 according to FIG. 4 provides a function of horizontally distributing the occlusal force of teeth in a radial form.

On the other hand, in case of the exposed portion 200 formed of a non-rigid material, when an occlusal force of teeth is exerted in the vertical direction of the implant 1, a diameter of a slit entrance portion of the flow groove 210, which is formed in a form of the slit 230, increases and decreases repeatedly and can elastically stretch. Accordingly, the exposed portion 200 can absorb the occlusal force of teeth.

Figure 5:
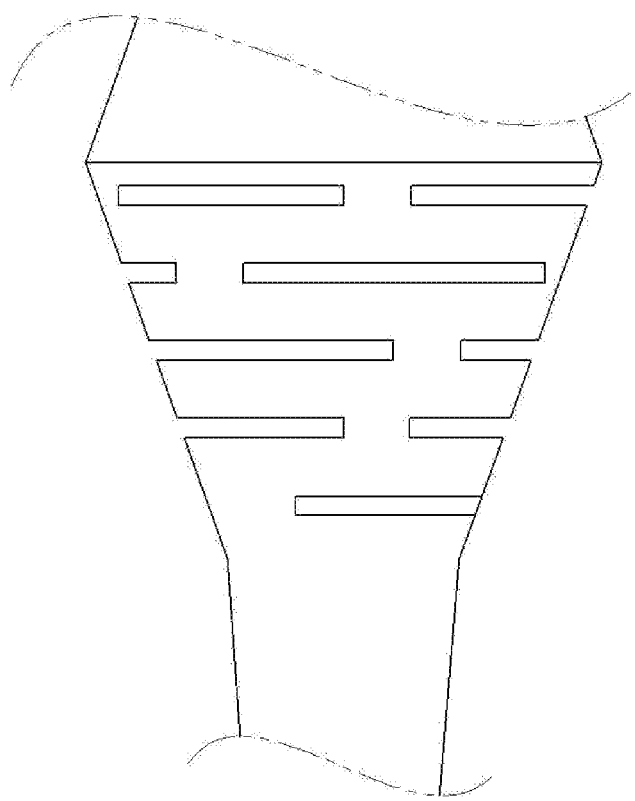
FIG. 5 is a front view illustrating a third modified embodiment of an implant abutment according to the present invention.

FIG. 5 is a front view illustrating a third modified embodiment of an implant abutment according to the present invention.

The flow groove 210 according to FIG. 5 is a groove extended by a certain length on a surface of the exposed portion 200. In the present invention, this structure is referred to as a horizontal slit 240.

The horizontal slit 240 is recessed and extended from the surface of the exposed portion 200 toward an inside of the exposed portion 200 in the horizontal direction of the exposed portion 200. The horizontal slit 240 may be plural, and horizontal slits 240 may be spaced apart from each other at a certain interval along the height direction of the exposed portion 200. In this case, it is desired that the horizontal slit 240 is recessed to the degree that the exposed portion 200 can maintain a thickness that can sufficiently support the artificial tooth 20 and the fixture 30. In addition, unlike the flow groove 210 of FIG. 4, the horizontal slit 240 may be formed on a specific surface with respect to the outer circumferential surface of the exposed portion 200.

According to this structure, when the occlusal force of teeth is exerted to the artificial tooth 20 in the vertical direction of the implant 1, the flow groove 210 according to FIG. 5 can distribute the occlusal force of teeth in the horizontal direction of the implant 1. In particular, unlike the structure shown in FIG. 4, the flow groove 210 of FIG. 5 is formed in a specific portion of the exposed portion 200, for example, in a portion corresponding to an outer side of an oral cavity, an inner side of the oral cavity, or a symmetrical side of the oral cavity, and thus, the flow groove 210 of FIG. 5 can distribute the occlusal force of teeth in a specific direction with respect to the outer circumferential surface.

That is, the flow groove 210 of FIG. 4 is capable of distributing the occlusal force of teeth in a radial form, whereas the flow groove 210 of FIG. 5, which is formed in a specific area, is capable of distributing the occlusal force of teeth in a specific direction.

Figure 6:
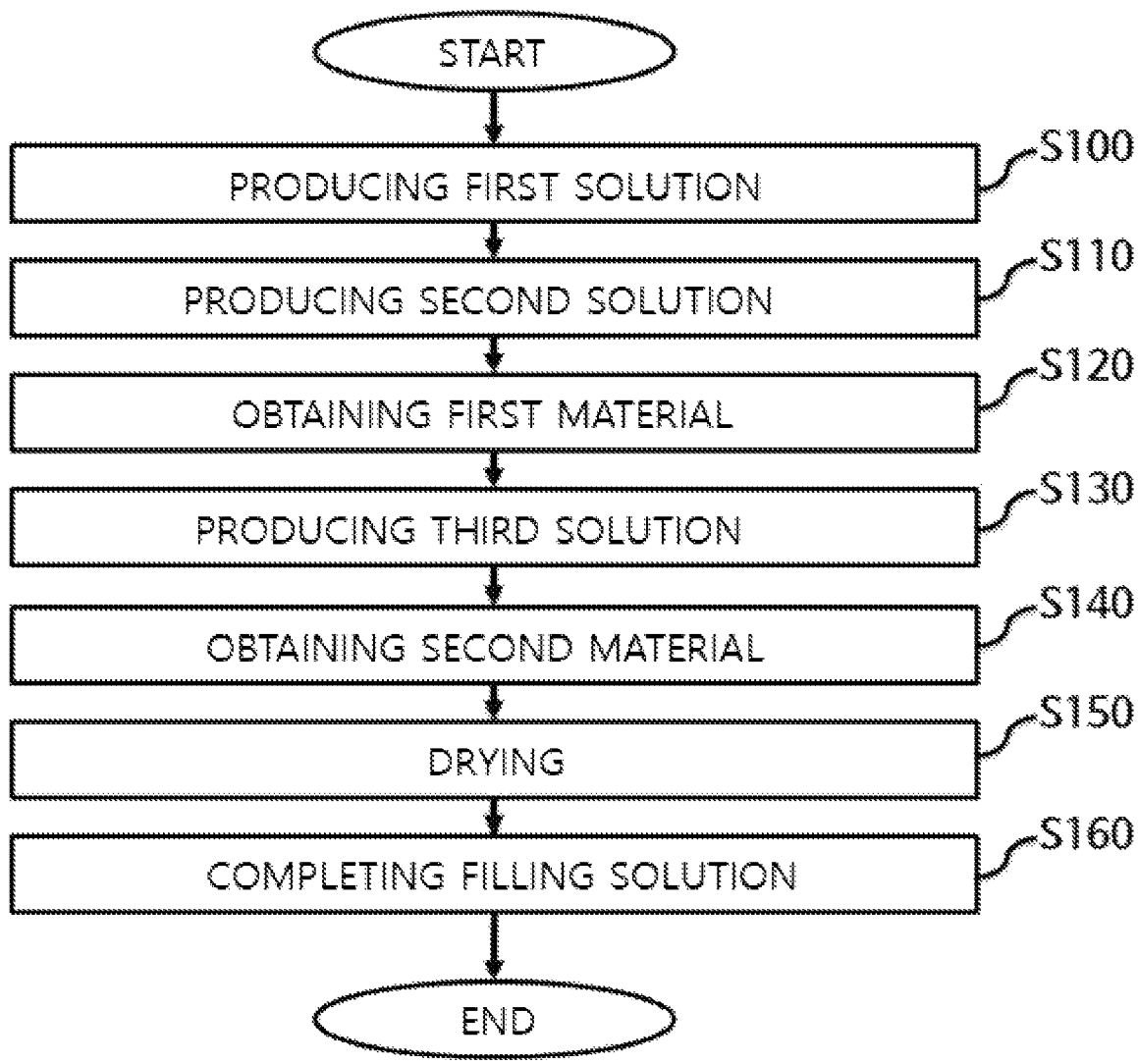
FIG. 6 is a flowchart illustrating a method for manufacturing a filling solution according to the present invention.

FIG. 6 is a flowchart illustrating a method for manufacturing a filling solution according to the present invention.

In this case, the flow groove 210 of the abutment 100 of the present invention may be filled with filler having an elasticity property, and accordingly, the filler can serve to assist elastic movement of the abutment 100 and buffer an external impact.

In addition, the filler may be a mixture of 10 to 30 wt % of a base material and 70 to 90 wt % of a filling solution containing sodium hyaluronate, based on a total weight of the filler. The filling solution can be solidified by irradiating ultraviolet rays for 2 to 10 minutes. In this case, the base material may be a material that has high elasticity such as silicone and is harmless to the human body and is preferably used in a state of a liquid material, a melted material, for mixing with the filling solution.

In addition, the filling solution may be solidified into a solid in a form of a gel by irradiating with ultraviolet rays and may further assist the elasticity and buffering property of the base material described above. In this case, although ultraviolet rays generally refer to electromagnetic waves with a wavelength of 397 to 1000 nm, in the present invention, it is desired to irradiate ultraviolet rays with a wavelength of 250 to 260 nm to solidify the filling solution.

In this case, in addition to the ultraviolet rays irradiation process, other processes such as cooling and drying may also be performed to solidify the base material.

The filling solution mentioned above may be manufactured through steps of: producing a first solution, producing a second solution, obtaining a first material, producing a third solution, obtaining a second material, drying, and completing the filling solution.

The step of producing a first solution is a process of mixing 95 to 99.9 wt % of water and 0.1 to 5 wt % of sodium hyaluronate based on a total weight of the first solution and then cooling to 0 to 10° C., to produce the first solution. After producing the first solution, it is desired to separately add sodium hydroxide to adjust a pH level of the first solution to 10. Here, sodium hyaluronate, also known as 'hyaluronic acid', is a mucopolysaccharide that is present in the body and harmless to the human body. Since sodium hyaluronate is harmless to the human body, it is generally used as a cosmetic ingredient or a material for health supplements. In addition, sodium hyaluronate can buffer external shocks and stimuli due to its high elastic property.

Next, the step of producing a second solution is a process of mixing 95 to 99.9 wt % of the first solution and 0.1 to 5 wt % of acrylyl chloride based on a total weight of the second solution, to produce the second solution. Then, the step of obtaining a first material is a process of filtering the second solution to obtain a filtrate from which impurities are removed, dialyzing the filtrate for 20 to 30 hours, and then freeze-drying, to obtain the first material. The step of obtaining a first material is preferably performed while maintaining a pH range of 9 to 10. Dialysis is a process of purifying a solution based on a principle that impurities mixed with small molecules or ions diffuse out of a membrane, and a purified first material can be obtained through the dialysis process. Through this process, acrylyl chloride may react with sodium hyaluronate described above and produce an acrylated hyaluronic acid material as the first material.

Then, the step of producing a third solution is a process of mixing 80 to 94 wt % of benzene anhydrous, 5 to 19 wt % of crosslinked polymer, 0.1 to 1 wt % of triethylamine, 0.1 to 1 wt % of acrylyl chloride, based on a total weight of the third solution in a nitrogen atmosphere to produce the third solution. The step of producing a third solution is preferably performed while stirring at a speed of 10,000 to 12,000 rpm. Here, the crosslinked polymer is added to provide crosslink and structural stability of the filling solution, and the filling solution may be crosslinked and solidified through an ultraviolet irradiation process to be described later. In this case, a natural polymer, a synthetic polymer, or a PEO-PPO-PEO (poly(ethylene oxide)-poly(propylene oxide)-poly(ethylene oxide)) triple block copolymer may be used as the crosslinked polymer. The crosslinked polymer may be structurally coupled to the first material to improve physical and structural stability and mechanical properties. In addition, for the crosslinking reaction between the first material and the crosslinked polymer, the acrylyl chloride may provide a vinyl functional group to the crosslinked polymer, and the triethylamine is added to promote the reaction between the crosslinked polymer and the acrylyl chloride.

Next, the step of obtaining a second material is a process of filtering the third solution to remove impurities, mixing 90 to 99 wt % of hexane and 1 to 10 wt % of the third solution from which impurities are removed, based on a total weight of a precipitation solution, and obtaining a precipitated second material. The step of drying is a process of washing the second material with water 2 to 5 times and then drying at 30 to 50° C. In this case, the second material may be produced as a precipitate by mixing the third solution with an excess of hexane, and this second material is a crosslinked polymer having a functional group modified by acrylyl chloride.

Lastly, the step of completing the filling solution is a process of mixing 85 to 95 wt % of PBS (Phosphate Buffer Saline), 0.5 to 5 wt % of the first material, 1 to 10 wt % of the second material, and 0.1 to 0.5 wt % of a photopolymerization initiator, based on a total weight of the filling solution. Here, PBS serves as a solvent for a reaction of the first material and the second material, and the photopolymerization initiator is added to solidify the filling solution to a filler when irradiating ultraviolet rays to the filling solution. In addition, the photopolymerization initiator is a material that initiates a polymerization reaction by absorbing energy from an irradiated ultraviolet light source. As the photopolymerization initiator, benzophenone, thioxantone, phenylglyoxylate, acyl phosphine oxide, or oximeester may be used, and a type of the photopolymerization initiator is not specifically limited as long as it can perform the functions described above.

The filling solution manufactured through this method may be mixed with the base material and then solidified by irradiating ultraviolet rays to become the filler. As described above, the solidified filler may assist the elastic movement of the abutment 100 and may assist to effectively reduce external impacts.

In addition, the filling solution may further include an elastic auxiliary agent containing 10 to 25 wt % of polycarbonate diol based on a total weight of the filling solution. Accordingly, the filler can have the further enhanced structural stability and absorbing ability of external shocks.

As described above, although the dental implant abutment according to the present invention has been explained in the description and illustrated in accompanying drawings, they are merely examples, and the spirit of the present invention is not limited to the above description and accompanying drawings. Various changes and modifications are possible without departing from the technical spirit of the present invention.

INDUSTRIAL APPLICABILITY

As described above, the dental implant abutment with an enhanced impact distribution function according to the present invention has the following useful effects and thus has a high industrial applicability. That is, by forming a plurality of grooves in the exposed portion of the implant abutment, the exposed portion performs a shock distribution function as if it shakes elastically, thereby providing a function of distributing an occlusal force of teeth exerted to the implant. In addition, by forming a groove in the exposed portion in a form of a screw thread, the exposed portion has an oblique structure to bypass an occlusal force of teeth in an oblique direction, thereby providing a function of effectively distributing the occlusal force of teeth in the oblique direction. Furthermore, by forming 3 to 4 grooves in the exposed portion in a form of a groove penetrating through the exposed portion, the grooves can provide a function of absorbing the occlusal force of teeth. Moreover, by forming grooves in the exposed portion in a form of a slit recessed along a horizontal direction of the exposed portion and arranging these slits to form a radial structure in the horizontal direction, an occlusal force of teeth can pass toward a radial direction, thereby providing a function of radially distributing the occlusal force of teeth in the horizontal direction. In addition, by filling a flow groove of the abutment with filler, the filler can support an elastic movement of the abutment and assist a function of buffering an external shock.

What is claimed is:

1. A dental implant abutment with an enhanced shock distribution function, the dental implant abutment comprising:
    an upper coupling portion that is an upper portion, the upper coupling portion being configured to be coupled to an artificial tooth;
    a lower coupling portion that is a lower portion, the lower coupling portion being configured to be coupled to a fixture, and
    an exposed portion that is disposed between the upper coupling portion and the lower coupling portion and has a flow groove filled with a filler,
    wherein the filler is a mixture of 10 to 30 wt % of a base material and 70 to 90 wt % of a filling solution containing sodium hyaluronate, based on a total weight of the filler, and the filling solution including an elastic auxiliary agent containing 10 to 25 wt % of polycarbonate diol based on a total weight of the filling solution.

2. The dental implant abutment of claim 1, wherein the flow groove is recessed in a form of a screw thread along an outer circumferential surface of the exposed portion.

3. The dental implant abutment of claim 1, wherein the flow groove includes:
    first plurality of slits recessed to a certain depth from an inner circumferential surface of the exposed portion to an outer circumferential surface of the exposed portion, and
    second plurality of slits recessed to a certain depth from the outer circumferential surface of the exposed portion to the inner circumferential surface of the exposed portion,
    wherein each of the first slits and each of the second slits are alternately formed along a height direction of the exposed portion in a repeated way and are spaced apart from each other by a certain height.

4. The dental implant abutment of claim 1, wherein the flow groove comprises a plurality of horizontal slits that extend from an outer circumferential surface of the exposed portion along a width direction of the exposed portion,
    wherein the horizontal slits are formed at regular intervals along a height direction of the exposed portion.

5. The dental implant abutment of claim 1, wherein the flow groove comprises a plurality of holes recessed in an outer circumferential surface of the exposed portion.

6. The dental implant abutment of claim 1, wherein the filling solution is manufactured through steps of:
    producing a first solution by mixing 95 to 99.9 wt % of water and 0.1 to 5 wt % of sodium hyaluronate based on a total weight of the first solution and then cooling the mixture of water and sodium to 0 to 10° C.;
    producing a second solution by mixing 95 to 99.9 wt % of the first solution and 0.1 to 5 wt % of acrylyl chloride based on a total weight of the second solution;
    obtaining a first material by filtering the second solution to obtain a filtrate from which impurities are removed, dialyzing the filtrate for 20 to 30 hours, and then freeze-drying the filtrate;
    producing a third solution by mixing 80 to 94 wt % of benzene anhydrous, 5 to 19 wt % of crosslinked polymer, 0.1 to 1 wt % of triethylamine, 0.1 to 1 wt % of acrylyl chloride, based on a total weight of the third solution, in a nitrogen atmosphere;
    obtaining a second material by filtering the third solution to remove impurities, mixing 90 to 99 wt % of hexane and 1 to 10 wt % of the third solution from which impurities are removed, based on a total weight of a precipitation solution, and obtaining a precipitated second material;
    drying by washing the second material with water 2 to 5 times and then drying the second material at 30 to 50° C., and
    completing the filling solution by mixing 85 to 95 wt % of PBS (Phosphate Buffer Saline), 0.5 to 5 wt % of the first material, 1 to 10 wt % of the second material, and 0.1 to 0.5 wt % of a photopolymerization initiator, based on a total weight of the filling solution.

* * * * *